(12) United States Patent
Small

(10) Patent No.: US 7,045,632 B2
(45) Date of Patent: May 16, 2006

(54) COMPOSITION AND METHOD FOR A HEXADENTATE LIGAND AND BIMETALLIC COMPLEX FOR POLYMERIZATION OF OLEFINS

(75) Inventor: Brooke L. Small, Kingwood, TX (US)

(73) Assignee: Chevron Phillips Chemical Company, LP, The Woodlands, TX (US)

(*) Notice: Subject to any disclaimer, the term of this patent is extended or adjusted under 35 U.S.C. 154(b) by 27 days.

(21) Appl. No.: 10/379,828

(22) Filed: Mar. 4, 2003

(65) Prior Publication Data
US 2004/0180778 A1 Sep. 16, 2004

(51) Int. Cl.
C07D 213/53 (2006.01)
C07D 401/02 (2006.01)

(52) U.S. Cl. .................................. 546/264; 526/265
(58) Field of Classification Search ............... 546/264; 526/265
See application file for complete search history.

(56) References Cited
U.S. PATENT DOCUMENTS
4,971,986 A * 11/1990 Stanek et al. ............... 514/357
(Continued)

FOREIGN PATENT DOCUMENTS
CN 1306014 1/2001
(Continued)

OTHER PUBLICATIONS
Kumar et al, Asian Journal of Chemistry, vol. 11, No. 3, pp. 964-969, 1999.*
(Continued)

Primary Examiner—Zinna Northington Davis
(74) Attorney, Agent, or Firm—Conley Rose, P.C.; Rodney B. Carroll; Joe D. Hulett

(57) ABSTRACT

A hexadentate ligand for polymerization of olefins including chemical structure I is provided:

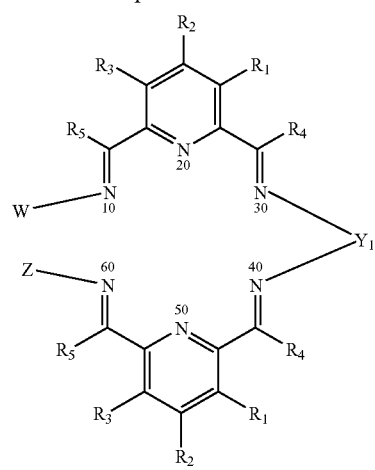

R1, R2, and R3 of chemical structure I are each independently hydrogen, hydrocarbyl, substituted hydrocarbyl, or an inert functional group; R4 and R5 are each independently hydrogen, hydrocarbyl, an inert functional group, or substituted hydrocarbyl; Y1 is a structural bridge; and W, Y1, and Z are independently hydrogen, hydrocarbyl, an inert functional group, or substituted hydrocarbyl having from about 0 to about 30 carbon atoms. In another embodiment of chemical structure I, W, $Y_1$, and Z are selected to produce chemical structure II:

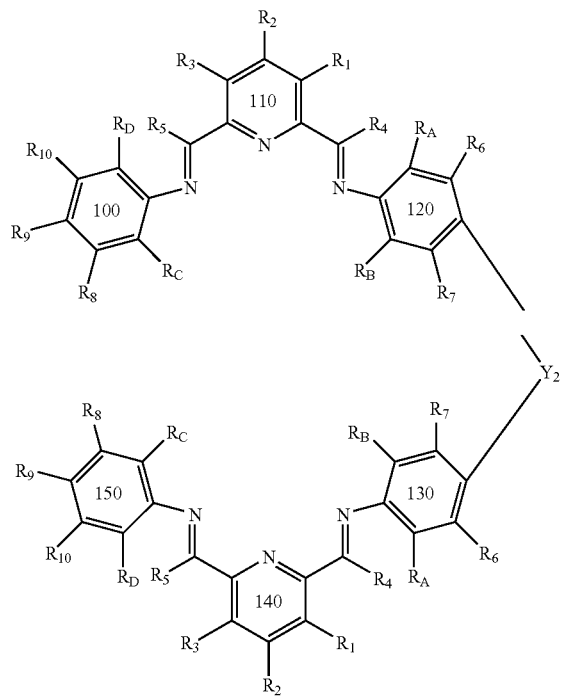

$R_6$, $R_7$, $R_8$, $R_9$, and $R_{10}$ of chemical structure II are each independently hydrogen, hydrocarbyl, an inert functional group, or substituted hydrocarbyl; $R_A$, $R_B$, $R_C$, and $R_D$ are each independently hydrogen, fluorine, an inert functional group, a primary carbon group, a secondary carbon group, or a tertiary carbon group; $Y_2$ is a structural bridge between two halves of the structure, and more particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring.

13 Claims, 1 Drawing Sheet

U.S. PATENT DOCUMENTS

| | | | |
|---|---|---|---|
| 5,955,555 A | 9/1999 | Bennett | 526/133 |
| 6,103,946 A | 8/2000 | Brookhart, III et al. | 585/523 |
| 6,214,761 B1 | 4/2001 | Bennett | 502/117 |
| 6,489,497 B1 | 12/2002 | Brookhart, III et al. | 556/138 |
| 2002/0028941 A1 | 3/2002 | De Boer et al. | 546/167 |
| 2003/0036615 A1 | 2/2003 | Brookhart, III et al. | 526/161 |
| 2003/0050494 A1 | 3/2003 | Brookhart, III et al. | 556/138 |

FOREIGN PATENT DOCUMENTS

| | | |
|---|---|---|
| EP | 1 229 020 A1 | 8/2002 |
| WO | WO01/10875 | 2/2001 |
| WO | WO01/58874 | 8/2001 |
| WO | WO02/00339 | 1/2002 |
| WO | WO02/28805 | 4/2002 |
| WO | WO03/011876 | 2/2003 |

OTHER PUBLICATIONS

Nelson et al, Journal of the Chemical Society, Dalton Transactions, Inorganic Chemistry, vol. 2, pp. 407-415, 1982.*

*Highly Active Iron and Cobalt Catalysts for the Polymerization of Ethylene*, Brooke L. Small, Maurice Brookhart, and Alison M.A. Bennett, *Journal of the American Chemical Society*, vol., 120, No. 16, pp. 4049-4050, 1998.

*Oligomerisation of Ethylene by Bis(imino)pyridyliron and -cobalt Complexes*, George J.P. Britovsek, et al., *Chem. Eur. J.*, vol. 6, No. 12, pp. 2221-2231, 2000.

*Iron-Based Catalysts with Exceptionally High Activities and Selectivities for Oligomerization of Ethylene to Linear a-Olefins*, Brooke L. Small and Maurice Brookhart, *Journal of the American Chemical Society*, vol. 120, No. 28, pp. 7143-7144, 1998.

International Search Report, PCT/US2004/004472, Jul. 16, 2004; 3 pages.

Li, Yuesheng et al.; Preparation of iron- or cobalt-based polynuclear pyridine-containing diimine catalysts for olefin polymerization; Database CAPLUS, XP-002284349; Aug. 1, 2001; 1 page.

* cited by examiner

COMPOSITION AND METHOD FOR A HEXADENTATE LIGAND AND BIMETALLIC COMPLEX FOR POLYMERIZATION OF OLEFINS

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present application relates generally to olefin oligomerization. More particularly, the present application relates to a novel hexadentate ligand, associated hexadentate bimetallic complex, and methods of making such hexadentate ligands and complexes. Additionally, the hexadentate ligand and complex are employed in the oligomerization of olefins.

BACKGROUND OF THE INVENTION

Olefins, also commonly known as alkenes, are important items of commerce. Their many applications include employment as intermediates in the manufacture of detergents, as more environmentally friendly replacements where refined oils might otherwise be used, as monomers, and as intermediates for many other types of products. An important subset of olefins are olefin oligomers, and one method of making olefin oligomers is via oligomerization of ethylene, which is a catalytic reaction involving various types of catalysts. Examples of catalysts used commercially in polymerization and oligomerization of olefins include alkylaluminum compounds, certain nickel-phosphine complexes, and a titanium halide with a Lewis acid, such as diethylaluminum chloride.

Another group of olefin polymerization catalysts is derived from pyridine bisimines. With catalysts of this type, a nitrogen-based ligand engages in a coordination reaction with a transition metal salt. The coordination reaction forms a metal complex, which is a catalyst precursor. The metal complex further reacts with another precursor or activator to generate a metal alkyl or metal hydride species. The catalyst resulting from the generation of the metal alkyl or metal hydride species polymerizes olefins.

Applications and demand for olefin polymers and oligomers continue to multiply, and competition to supply them correspondingly intensifies. Thus, additional novel and improved catalysts and methods for olefin polymerization and oligomerization are desirable.

SUMMARY OF THE INVENTION

A hexadentate ligand for polymerization of olefins including chemical structure I is provided:

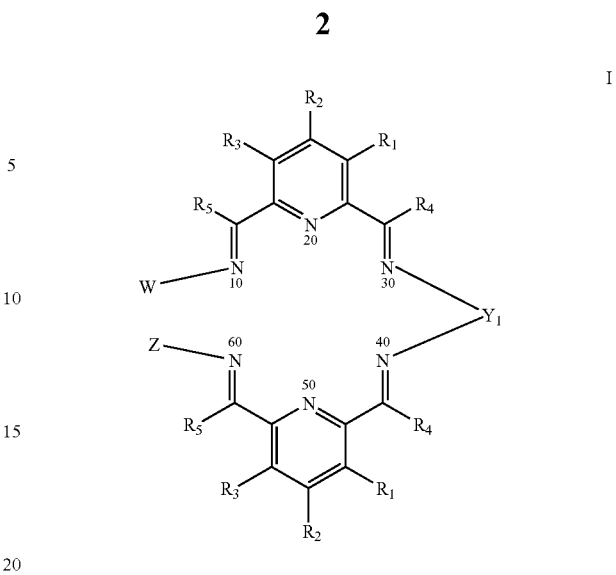

$R_1$, $R_2$, and $R_3$ of chemical structure I are each independently hydrogen, hydrocarbyl, substituted hydrocarbyl, or an inert functional group; $R_4$ and $R_5$ are each independently hydrogen, hydrocarbyl, an inert functional group, or substituted hydrocarbyl; $Y_1$ is a structural bridge; and W, $Y_1$, and Z are independently hydrogen, hydrocarbyl, an inert functional group, or substituted hydrocarbyl having from about 0 to about 30 carbon atoms. In an embodiment of chemical structure I, the groups W, $Y_1$, and Z are selected such that an activated transition metal complex of the ligand, in the presence of one or more monomers under suitable polymerization conditions, results in a polymerization product having greater than about 50 weight percent oligomers having from about 4 to about 30 carbon atoms. In another embodiment, chemical structure I includes a mirror plane. In another embodiment of chemical structure I, the groups W, $Y_1$, and Z are selected to produce chemical structure II:

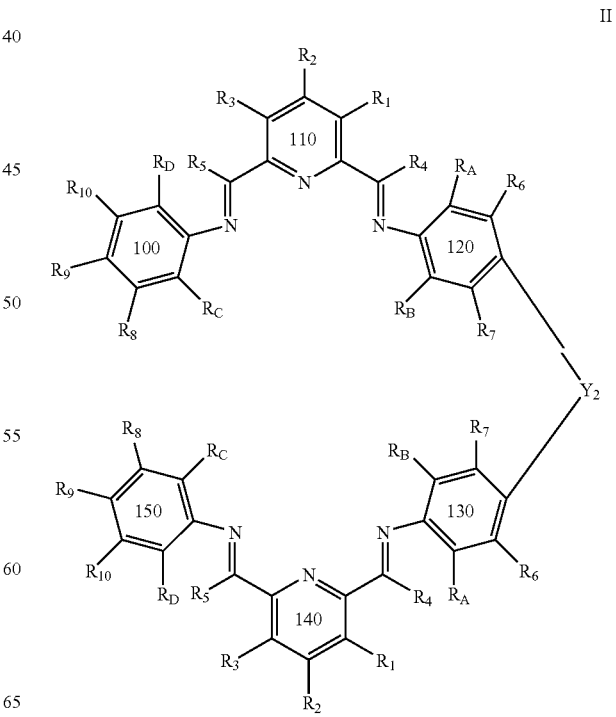

$R_6$, $R_7$, $R_8$, $R_9$, and $R_{10}$ of chemical structure II are each independently hydrogen, hydrocarbyl, an inert functional group, or substituted hydrocarbyl; $R_A$, $R_B$, $R_C$, and $R_D$ are each independently hydrogen, fluorine, an inert functional group, a primary carbon group, a secondary carbon group, or a tertiary carbon group; $Y_2$ is a structural bridge between two halves of the structure, and more particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring.

In another embodiment, a hexadentate bimetallic complex having chemical structure III, and method of producing same, is provided:

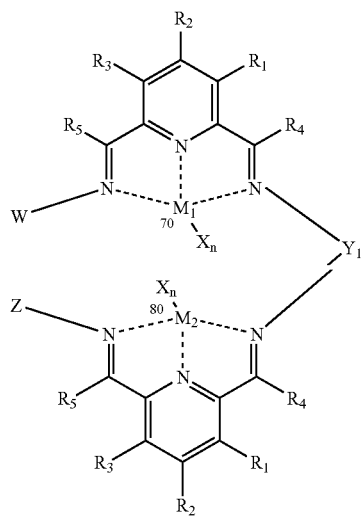

III

R1, R2, R3, R4, R5, W, Z, and Y1 are as defined above for chemical structure I. $M_1$ and $M_2$ are metal atoms that may be independently selected from the group consisting of cobalt, iron, chromium, and vanadium; each X may be an anion, such as a halide or acetyl acetonate, so that the total number of negative charges on X is equal to the oxidation state of $M_1$ or $M_2$; and n is 1, 2, or 3, so that the total number of negative charges on X is equal to the oxidation state of $M_1$ or $M_2$.

In another embodiment, a hexadentate bimetallic complex having chemical structure IV, and method of producing same, is provided:

IV

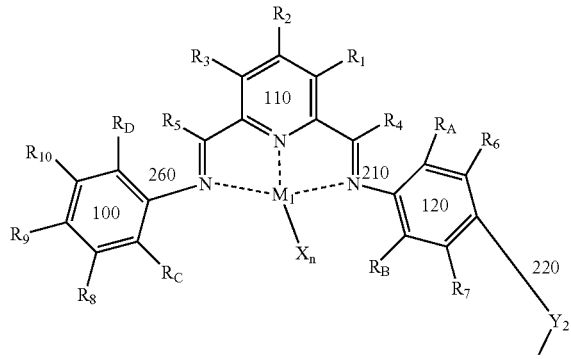

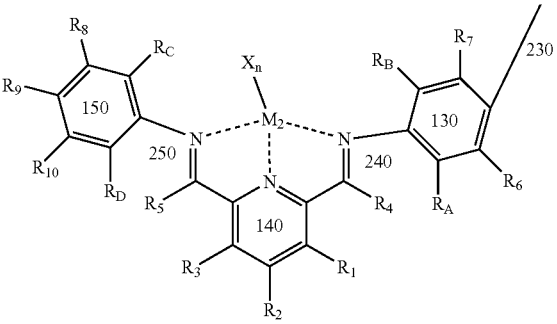

The method for producing chemical structure IV includes mixing a pyridine compound having chemical structure V:

V

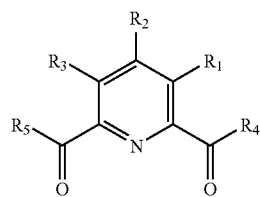

with a substituted arylene diamine having chemical structure VI:

VI

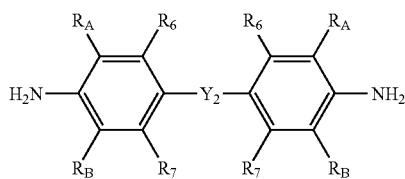

and a substituted aryl amine having chemical structure VII:

VII

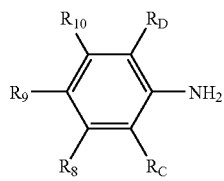

in a suitable solvent; and adding at least one metal salt of the formula $MX_n$. $R_1$, $R_2$, and $R_3$ of chemical structure IV are each independently hydrogen, hydrocarbyl, substituted hydrocarbyl, or an inert functional group; $R_4$ and $R_5$ are each independently hydrogen, hydrocarbyl, an inert functional group, or substituted hydrocarbyl; $R_6$, $R_7$, $R_8$, $R_9$, and $R_{10}$ are each independently hydrogen, hydrocarbyl, an inert functional group, or substituted hydrocarbyl; $R_A$, $R_B$, $R_C$, and $R_D$ are each independently hydrogen, fluorine, an inert functional group, a primary carbon group, a secondary carbon group, or a tertiary carbon group; $Y_2$ is a structural bridge between two halves of the structure, and more particularly may be a bond, a hydrocarbyl group comprising from about 0 to about 20 carbon atoms, methylene (CH$_2$), ethylene (C$_2$H$_4$), or an inert functional group; any two of R$_4$, R$_6$, R$_7$, R$_B$, R$_C$, R$_8$, R$_9$, R$_{10}$, and R$_D$, or any portion of Y$_2$, vicinal to one another, taken together may form a ring; M$_1$ and M$_2$ are independently selected metal atoms that are selected from a group comprising cobalt, iron, chromium, and vanadium; each X is an anion; and n is 1, 2, or 3, so that the total number of negative charges on X is equal to the oxidation state of M$_1$ or M$_2$.

In another embodiment, a method for preparing a polymerization catalyst system is provided. Such method includes executing a coordination reaction between a hexadentate ligand having chemical structure II:

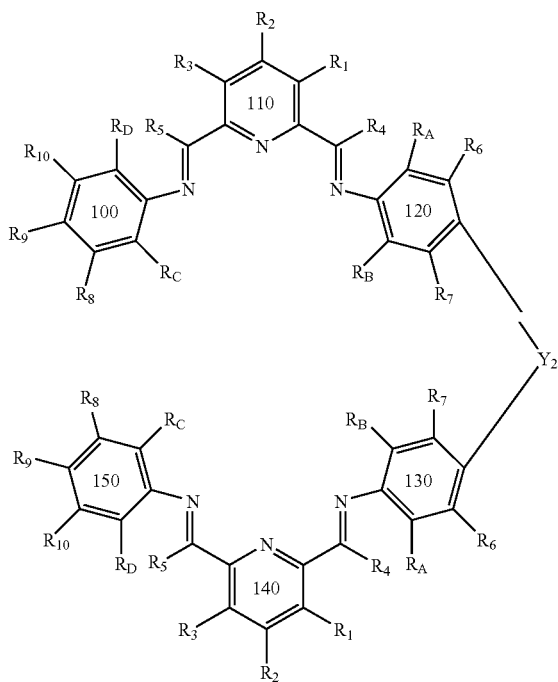

II and a metal salt of the formula MX$_n$, to form a hexadentate bimetallic complex having chemical structure IV:

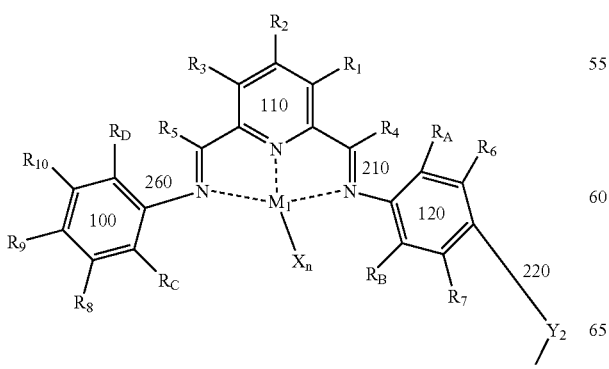

IV

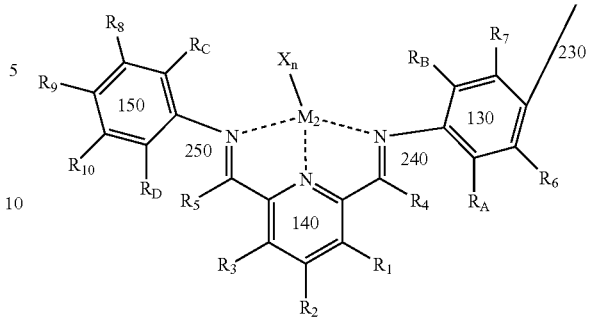

-continued

The method also includes generating a metal alkyl or metal hydride species; and contacting the catalyst system with one or more monomers under suitable reaction conditions to polymerize the monomer. R$_1$, R$_2$, and R$_3$ of chemical structures II and IV are each independently hydrogen, hydrocarbyl, substituted hydrocarbyl, or an inert functional group; R$_4$ and R$_5$ are each independently hydrogen, hydrocarbyl, an inert functional group, or substituted hydrocarbyl; R$_6$, R$_7$, R$_8$, R$_9$, and R$_{10}$ are each independently hydrogen, hydrocarbyl, an inert functional group, or substituted hydrocarbyl; R$_A$, R$_B$, R$_C$, and R$_D$ are each independently hydrogen, fluorine, an inert functional group, a primary carbon group, a secondary carbon group, or a tertiary carbon group; Y$_2$ is a structural bridge between two halves of the structure, and more particularly may be a bond, a hydrocarbyl group comprising from about 0 to about 20 carbon atoms, methylene (CH$_2$), ethylene (C$_2$H$_4$), or an inert functional group; any two of R$_4$, R$_6$, R$_7$, R$_B$, R$_C$, R$_8$, R$_9$, R$_{10}$, and R$_D$, or any portion of Y$_2$, vicinal to one another, taken together may form a ring; M$_1$ and M$_2$ are independently selected metal atoms that are selected from a group comprising cobalt, iron, chromium, and vanadium; each X is an anion; n is 1, 2, or 3, so that the total number of negative charges on X is equal to the oxidation state of M$_1$ or M$_2$; and olefins may or may not be present at the step of generating a metal alkyl or metal hydride species.

DETAILED DESCRIPTION OF EMBODIMENTS

Figure 1:
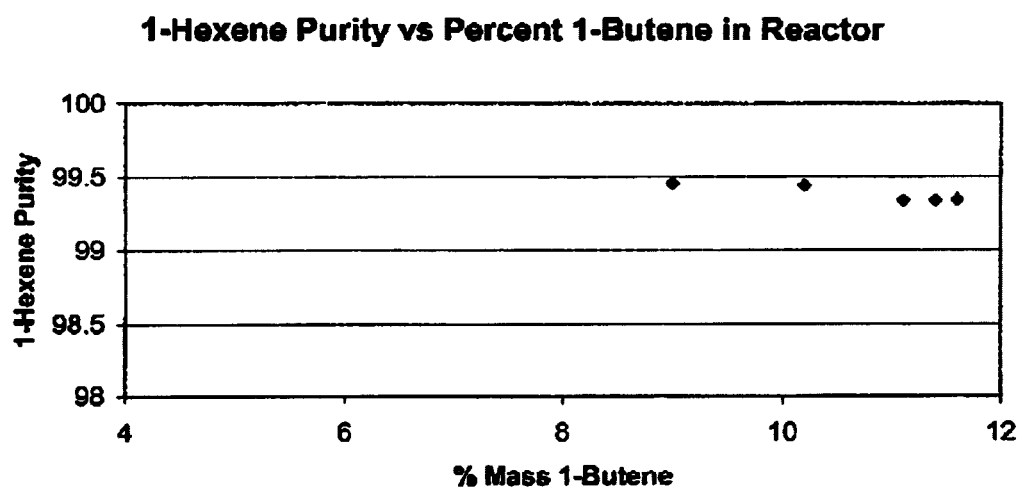
FIG. 1 is a chart illustrating the catalyst's high selectivity for ethylene relative to higher olefins.

The present application discloses a hexadentate ligand (or "ligand"), illustrated by chemical structure I, that is employed in the making of catalysts for polymerizing and oligomerizing olefins.

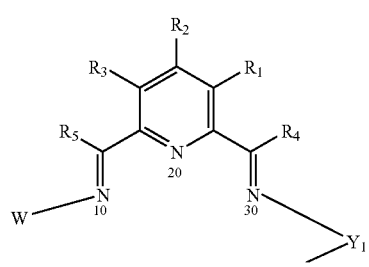

I

-continued

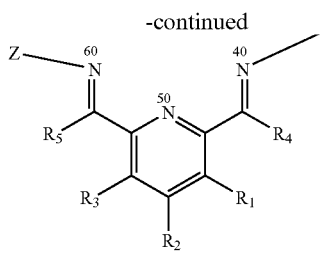

Embodiments of the various types and combinations of "R" groups are defined below. The hexadentate ligand structure may be identified by six nitrogens denoted by reference numerals 10, 20, 30, 40, 50, and 60, wherein the ligand may be viewed as consisting of two halves or sides; one side including nitrogen groups 10, 20, and 30, and the other side including nitrogen groups 40, 50, and 60. The two halves are connected by a structural bridge $Y_1$. When producing a metal complex from the hexadentate ligand, the ligand is reacted with the salt of a transition metal. A coordination reaction between the hexadentate ligand of chemical structure I and a metal salt forms a hexadentate bimetallic complex (or "complex"), such as the one illustrated by chemical structure III, which includes two different sites 70 and 80 where the metal salt may coordinate with the ligand. The hexadentate bimetallic complex of chemical structure III is a precursor to the catalyst for polymerizing and oligomerizing olefins.

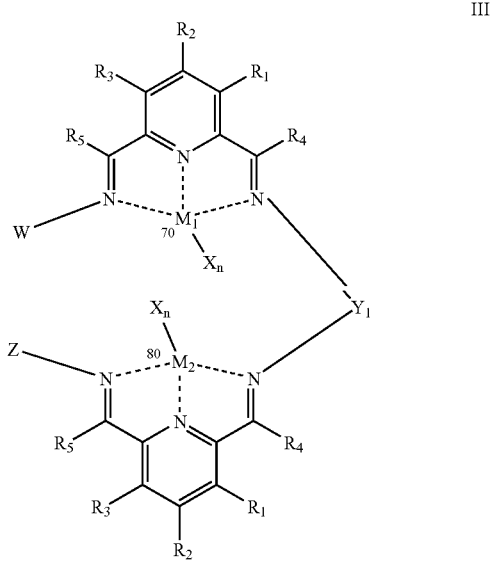

In an embodiment, the components of the hexadentate ligand of structure I and hexadentate bimetallic complex of structure III, labeled as $R_1$, $R_2$, $R_3$, $R_4$, $R_5$, W, $Y_1$, Z, M, and $X_n$ are as follows:

$R_1$, $R_2$, and $R_3$ are each independently hydrogen, hydrocarbyl, substituted hydrocarbyl, or an inert functional group, as defined below;

$R_4$ and $R_5$ are each independently hydrogen, hydrocarbyl, an inert functional group, or substituted hydrocarbyl;

$Y_1$ is a structural bridge between the two halves of the ligand and may be a bond between nitrogen group 30 and nitrogen group 40; or $Y_1$ is a structural bridge wherein $Y_1$, W, and Z are each independently hydrogen, hydrocarbyl, an inert functional group, or substituted hydrocarbyl including from about 0 to about 30 carbon atoms;

$M_1$ and $M_2$ are metal atoms that may be independently selected from the group consisting of cobalt, iron, chromium, and vanadium;

each X may be an anion, such as a halide or acetyl acetonate, so that the total number of negative charges on X is equal to the oxidation state of $M_1$ or $M_2$; and n is 1, 2, or 3, so that the total number of negative charges on X is equal to the oxidation state of $M_1$ or $M_2$.

In an embodiment of the ligand and complex of structures I and III, $R_1$, $R_2$, $R_3$, $R_4$, and $R_5$ are defined as above; and W, $Y_1$, and Z are selected such that an activated transition metal complex of the ligand, in the presence of one or more monomers under suitable polymerization conditions, results in a polymerization product having greater than about 50 weight percent oligomers having from about 4 to about 30 carbon atoms. In another embodiment, each half of the hexadentate ligand of chemical structure I and each half of the hexadentate complex of chemical structure III is a mirror image of the other. The two halves, one denoted by nitrogen groups 10, 20, and 30, and the other denoted by nitrogen groups 40, 50, and 60, are divided by a mirror plane that passes through $Y_1$. In yet other embodiments of the ligand of structure I and complex of structure II, the structural bridge $Y_1$ may be cyclohexane.

In an embodiment of the hexadentate ligand illustrated by structure I, the groups W, $Y_1$, and Z are selected to produce the hexadentate ligand illustrated by chemical structure II:

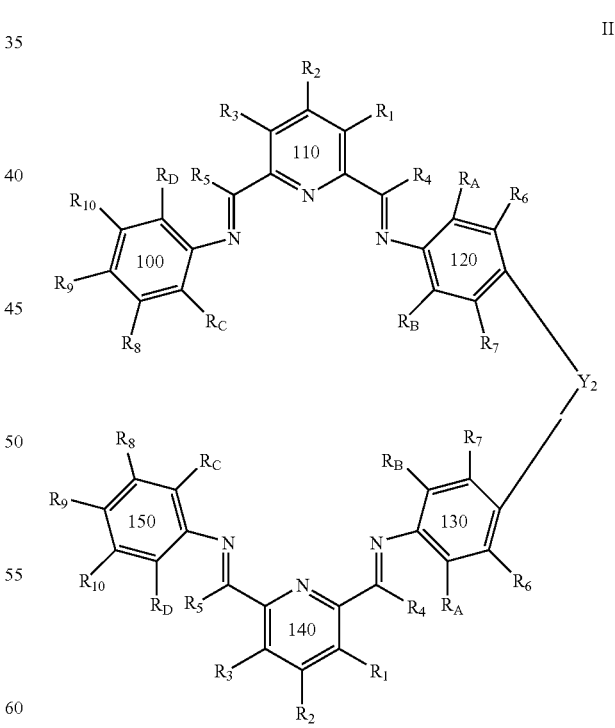

When preparing a catalyst for olefin polymerization or oligomerization, the hexadentate ligand illustrated by structure II is reacted with a metal salt such that a coordination reaction results in the hexadentate bimetallic complex of structure IV:

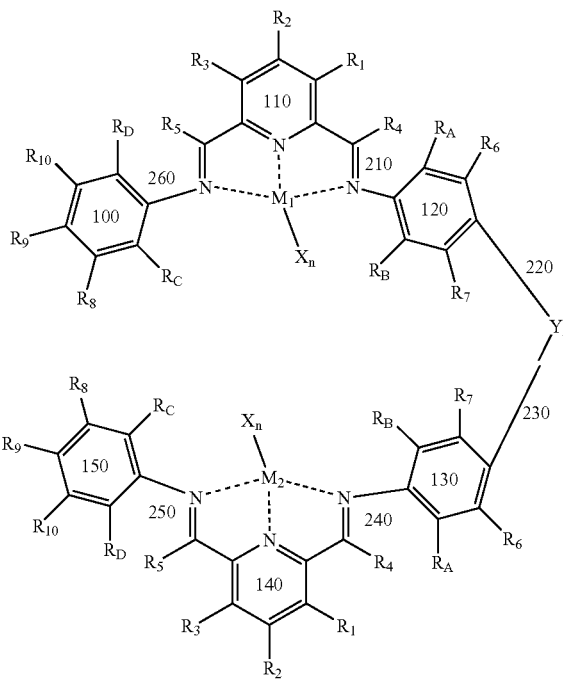

IV

The groups $R_A$, $R_B$, $R_C$, and $R_D$ are ortho to the amines. In an embodiment of the hexadentate ligand II and complex IV, the following pendant groups are defined:

$R_1$, $R_2$, and $R_3$ are each independently hydrogen, hydrocarbyl, substituted hydrocarbyl, or an inert functional group, as defined below;

$R_4$ and $R_5$ are each independently hydrogen, hydrocarbyl, an inert functional group, or substituted hydrocarbyl;

$R_6$, $R_7$, $R_8$, $R_9$, and $R_{10}$ are each independently hydrogen, hydrocarbyl, an inert functional group, or substituted hydrocarbyl, as defined below;

$R_A$, $R_B$, $R_C$, and $R_D$ are independently selected from hydrogen, fluorine, an inert functional group, a primary carbon group, a secondary carbon group, or a tertiary carbon group;

$M_1$ and $M_2$ are metal atoms that may be independently selected from the group consisting of cobalt, iron, chromium, and vanadium;

each X may be an anion such as a halide or acetyl acetonate, so that the total number of negative charges on X is equal to the oxidation state of $M_1$ or $M_2$;

n is 1, 2, or 3, so that the total number of negative charges on X is equal to the oxidation state of $M_1$ or $M_2$;

$Y_2$ is generally a structural bridge between two halves of the structure, and more particularly may be a bond between rings 120 and 130, a hydrocarbyl group including from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, $R_D$, and any portion of $Y_2$, vicinal to one another, taken together may form a ring.

In another embodiment of the hexadentate ligand II and complex IV, the pendant groups are as defined above, with the exception that:

when $R_A$ is a primary carbon group, then none, one, or two of $R_B$, $R_C$, and $R_D$ are primary carbon groups, secondary carbon groups, phenyl, substituted phenyl, or inert functional groups, and the remainder of $R_B$, $R_C$, and $R_D$ are hydrogen or fluorine; or when $R_A$ is a secondary carbon group, then none, one, or two of $R_B$, $R_C$ and $R_D$ are primary carbon groups, secondary carbon groups, phenyl, substituted phenyl, or inert functional groups, and the remainder of $R_B$, $R_C$, and $R_D$ are hydrogen or fluorine; or when $R_A$ is a tertiary carbon group, then none or one of $R_B$, $R_C$, and $R_D$ are tertiary, phenyl, or substituted phenyl, and the remainder are hydrogen or fluorine; and when $R_C$ is a primary carbon group, then none, one, or two of $R_A$, $R_B$, and $R_D$ are primary carbon groups, secondary carbon groups, phenyl, substituted phenyl, or inert functional groups, and the remainder of $R_A$, $R_B$, and $R_D$ are hydrogen or fluorine; or when $R_C$ is a secondary carbon group, then none, one, or two of $R_A$, $R_B$ and $R_D$ are primary carbon groups, secondary carbon groups, phenyl, substituted phenyl, or inert functional groups, and the remainder of $R_A$, $R_B$, and $R_D$ are hydrogen or fluorine; or when $R_C$ is a tertiary carbon group, then none or one of $R_A$, $R_B$, and $R_D$ are tertiary, phenyl, or substituted phenyl, and the remainder of $R_A$, $R_B$, and $R_D$ are hydrogen or fluorine.

In an embodiment, the ligand II and complex IV may be viewed as consisting of two halves or sides; one side including rings 100, 110, and 120, and the other side including rings 130, 140, and 150. The two halves are connected by a structural bridge $Y_2$. In another embodiment, one side of the hexadentate structure identified by rings 100, 110, and 120 is a mirror image of the other half of the structure, which is identified by rings 130, 140, and 150. The two halves or sides of the structure are divided by a mirror plane, which passes through $Y_2$. In another embodiment, $Y_2$ connects rings 120 and 130 at their respective meta positions and the $R_7$ groups are located at the respective para positions.

Referring to the hexadentate complex IV, other distinctive embodiments of the ligand and complex may result because the rings 100, 120, 130, and 150 may rotate at their chemical bonds. For example, the ring 130 may rotate at its bonds 230 and/or 240 such that the resultant ligand or complex is not a true mirror image. In the case of a 180 degree rotation of the ring 130 along the bonds 230 and 240, as illustrated, the groups $R_A$ and $R_6$ may rotate to the inside of the structure, and the groups $R_B$ and $R_7$ may rotate to the outside of the structure. Similarly, ring 100 may rotate along bond 260; ring 120 may rotate along bonds 210 and 220; ring 130 may rotate along bonds 230 and 240; and/or ring 150 may rotate along bond 250.

In another embodiment of the ligand II and complex IV, $R_A$, $R_B$, $R_C$, and $R_D$ are selected such that an activated transition metal complex, in the presence of one or more monomers under suitable polymerization conditions, results in a polymerization product having greater than about 50 weight percent oligomers having from about 4 to about 30 carbon atoms.

In the following embodiments, unless otherwise specified, all groups other than the key pendant groups are as defined above. In an embodiment of the ligand II and complex IV, $R_A$ and $R_B$ are hydrogen; and $R_C$ and $R_D$ are each independently methyl, ethyl, propyl, or isopropyl. In an embodiment, $R_A$ and $R_B$ are methyl; and $R_C$ and $R_D$ are each independently methyl, ethyl, propyl, or isopropyl. In an embodiment, $R_C$ and $R_D$ are hydrogen; and $R_A$ and $R_B$ are each independently methyl, ethyl, propyl, or isopropyl. In an embodiment, $R_C$ and $R_D$ are methyl; and $R_A$ and $R_B$ are each independently methyl, ethyl, propyl, or isopropyl. In an embodiment, $R_A$ and $R_D$ are hydrogen; and $R_B$ and $R_C$ are each independently methyl, ethyl, propyl, or isopropyl. In an embodiment, $R_A$ and $R_D$ are methyl; and $R_B$ and $R_C$ are each independently methyl, ethyl, propyl, or isopropyl.

In an embodiment of a hexadentate bimetallic complex III or IV, pendant groups may be as defined above, except that both $M_1$ and $M_2$ are cobalt. In another embodiment, both $M_1$ and $M_2$ are iron. In another embodiment, one of the metal atoms, $M_1$ or $M_2$, is iron, and the other is cobalt. In another embodiment, selection of $M_1$ and $M_2$ affects selection of $R_A$, $R_B$, $R_C$, $R_D$, W, $Y_1$, and Z.

In an embodiment of a hexadentate bimetallic complex III or IV, including pendant groups as defined above, an activated complex results in an alpha olefin product having greater than about 80 percent 1-alkene content.

In an embodiment of a complex IV, pendant groups may be as defined above, with the following exceptions:
$R_1$, $R_2$, and $R_3$ are hydrogen;
$R_4$ and $R_5$ are methyl or hydrogen;
$R_6$, $R_7$, $R_8$, $R_9$, and $R_{10}$ are hydrogen; and
$R_A$, $R_B$, $R_C$, and $R_D$ are each independently methyl, ethyl, propyl, or isopropyl.

In the following embodiments of a complex IV, pendant groups may be as defined above, except that $M_1$ and $M_2$ are iron, and $R_4$ and $R_5$ are methyl. In an embodiment, $R_A$ and $R_B$ are hydrogen, and $R_C$ and $R_D$ are methyl. In an embodiment, $R_A$ and $R_B$ are methyl, and $R_C$ and $R_D$ are hydrogen. In another embodiment, $R_A$ and $R_C$ are methyl, and $R_B$ and $R_D$ are hydrogen.

For purposes of this application, a hydrocarbyl group is a group containing only carbon and hydrogen. If not otherwise stated, it is preferred that hydrocarbyl groups herein contain 1 to about 30 carbon atoms. The terms "hydrocarbyl" and "alkyl" are equivalent, and may be used interchangeably.

For purposes of this application, a substituted hydrocarbyl is a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

For purposes of this application, an inert functional group is a group, other than hydrocarbyl or substituted hydrocarbyl, which does not substantially interfere with any process described herein where the compound in which it is present takes part. Examples of inert functional groups include halo (fluoro, chloro, bromo and iodo), or ethers such as —$OR_{18}$ wherein $R_{18}$ is hydrocarbyl or substituted hydrocarbyl. In cases in which the functional group may be near a metal atom, such as $R_4$, $R_5$, $R_8$, $R_B$, $R_C$, and $R_D$ the functional group should not coordinate to the metal atom more strongly than the groups in compounds containing $R_4$, $R_5$, $R_8$, $R_B$, $R_C$ and $R_D$ which are shown as coordinating to the metal atom, that is they should not displace the desired coordinating group.

For purposes of this application, a primary carbon group includes a group of the formula —$CH_2$—, wherein the free valence is to any other atom (the bond represented by the hyphen is to the benzene ring to which the primary carbon group is attached). Thus, the free valence may be bonded to a hydrogen atom, halogen atom, carbon atom, oxygen atom, sulfur atom, etc. In other words, the free valence may be to hydrogen, hydrocarbyl, substituted hydrocarbyl or a functional group. Examples of primary carbon groups include —$CH_3$, —$CH_2CH(CH_3)_2$, —$CH_2Cl$, —$CH_2C_6H_5$, and —$CH_2OCH_3$.

For purposes of this application, a secondary carbon group includes a group of the formula —CH=, wherein the free valences are to any other atoms (the bond represented by the hyphen is to the benzene ring to which the secondary carbon group is attached). Thus, the free valences may be bonded to a hydrogen atom, halogen atom, carbon atom, oxygen atom, sulfur atom, etc. In other words, the free valences may be to hydrogen, hydrocarbyl, substituted hydrocarbyl or a functional group. Specific examples of secondary carbon groups include —$CH(CH_3)_2$, —$CHCl_2$, —$CH(C_6H_5)_2$, cyclohexyl, —$CH(CH_3)OCH_3$, and —CH=$CHCH_3$.

For purposes of this application, a tertiary carbon group includes a group of the formula —C≡, wherein the free valences are to any other atoms. Thus, the free valences may be bonded to a hydrogen atom, halogen atom, carbon atom, oxygen atom, sulfur atom, etc. In other words, the free valences may be to hydrogen, hydrocarbyl, substituted hydrocarbyl or a functional group. Examples of tertiary carbon groups include: —$C(CH_3)_3$, —$C(C_6H_5)_3$, —$CCl_3$, —$C(CH_3)_2OCH_3$, —C≡CH, —$C(CH_3)CH$=$CH_2$, $C_6H_5$, $CF_3$, and 1-adamantyl.

In an embodiment, a method for producing a hexadentate bimetallic complex is provided. The method comprises mixing a pyridine compound having chemical structure V:

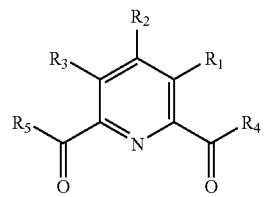

V with a substituted arylene diamine having chemical structure VI:

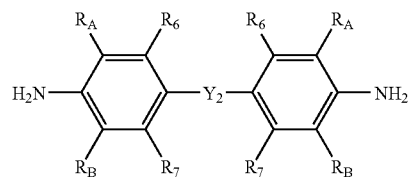

VI and a substituted aryl amine having chemical structure VII:

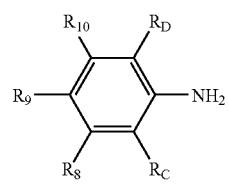

VII

The compounds having chemical structures V, VI, and VII may be mixed in a suitable solvent, as those are commonly known in the art. In an embodiment, the hexadentate ligand and bimetallic complex may be made up of the compounds having chemical structures V, VI, and VII in the following ratios: 2 parts chemical structure V, 1 part chemical structure VI, and 2 parts chemical structure VII. In an embodiment, the relative amounts of the compounds and order of mixing the compounds may be selected in order to maximize the yield of the hexadentate ligand of structure II. Subsequently, a metal salt of the form $MX_n$, as defined above, may be added to the mixture forming a hexadentate bimetallic complex having chemical structure III or IV. In an embodiment, the pendant groups of complex III or IV formed by the above method may be defined as follows:

$R_1$, $R_2$, and $R_3$ are each independently hydrogen, hydrocarbyl, substituted hydrocarbyl, or an inert functional group, as defined below;

$R_4$ and $R_5$ are each independently hydrogen, hydrocarbyl, an inert functional group, or substituted hydrocarbyl;

$R_6$, $R_7$, $R_8$, $R_9$, and $R_{10}$ are each independently hydrogen, hydrocarbyl, an inert functional group, or substituted hydrocarbyl, as defined below;

$R_A$, $R_B$, $R_C$, and $R_D$ are independently selected from hydrogen, fluorine, an inert functional group, a primary carbon group, a secondary carbon group, or a tertiary carbon group;

$M_1$ and $M_2$ are metal atoms that may be independently selected from the group consisting of cobalt, iron, chromium, and vanadium;

each X may be an anion such as a halide or acetyl acetonate, so that the total number of negative charges on X is equal to the oxidation state of $M_1$ or $M_2$;

n is 1, 2, or 3, so that the total number of negative charges on X is equal to the oxidation state of $M_1$ or $M_2$;

$Y_2$ is generally a structural bridge between two halves of the structure, and more particularly may be a bond between rings 120 and 130, a hydrocarbyl group including from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, $R_D$, and any portion of $Y_2$, vicinal to one another, taken together may form a ring.

In an embodiment of the above method, a hexadentate ligand having chemical structure I or II is formed as an intermediate that may be involved in a coordination reaction to produce a hexadentate bimetallic complex having chemical structure III or IV. In another embodiment of the above method, a hexadentate ligand having chemical structure II is formed as an intermediate, wherein ligand purity is at least about 90 percent when measured by nuclear magnetic resonance spectroscopy (NMR). In another embodiment, the two halves of the hexadentate ligand and complex formed by the above method are divided by a mirror plane. In another embodiment, the pendant groups are as defined in the above method, except that:

M1 and M2 are iron;

when $R_A$ is a primary carbon group, then none, one, or two of $R_B$, $R_C$, and $R_D$ are primary carbon groups, secondary carbon groups, phenyl, substituted phenyl, or inert functional groups, and the remainder of $R_B$, $R_C$, and $R_D$ are hydrogen or fluorine; or when $R_A$ is a secondary carbon group, then none, one, or two of $R_B$, $R_C$ and $R_D$ are primary carbon groups, secondary carbon groups, phenyl, substituted phenyl, or inert functional groups, and the remainder of $R_B$, $R_C$, and $R_D$ are hydrogen or fluorine; or when $R_A$ is a tertiary carbon group, then none or one of $R_B$, $R_C$, and $R_D$ are tertiary, phenyl, or substituted phenyl, and the remainder are hydrogen or fluorine; and when $R_C$ is a primary carbon group, then none, one, or two of $R_A$, $R_B$, and $R_D$ are primary carbon groups, secondary carbon groups, phenyl, substituted phenyl, or inert functional groups, and the remainder of $R_A$, $R_B$, and $R_D$ are hydrogen or fluorine; or when $R_C$ is a secondary carbon group, then none, one, or two of $R_A$, $R_B$ and $R_D$ are primary carbon groups, secondary carbon groups, phenyl, substituted phenyl, or inert functional groups, and the remainder of $R_A$, $R_B$, and $R_D$ are hydrogen or fluorine; or when $R_C$ is a tertiary carbon group, then none or one of $R_A$, $R_B$, and $R_D$ are tertiary, phenyl, or substituted phenyl, and the remainder of $R_A$, $R_B$, and $R_D$ are hydrogen or fluorine.

In another embodiment, the order of mixing of the arylene diamine and the substituted aryl amine may be dictated by the hexadentate bimetallic complex desired. In another embodiment, $R_A$, $R_B$, $R_C$, and $R_D$ are selected such that an activated transition metal complex of the ligand, in the presence of one or more monomers under suitable polymerization conditions, results in a polymerization product having greater than about 50 weight percent oligomers having from about 4 to about 30 carbon atoms. In another embodiment, the activated complex formed by the above method produces alpha olefins having greater than about 80 percent 1-alkene content. In other embodiments, the pendant groups (including R, W, X, Y, Z, and M groups) of chemical structures V, VI, and VII may be selected such that the hexadentate bimetallic complexes resulting from the above method conform to the various combinations defined above for the ligands and complexes having chemical structures I, II, III and IV.

In various embodiments, the above method produces the related and desirable ligands and complexes of Table 1:

| NUMBER | STRUCTURE |
|---|---|
| VIII | 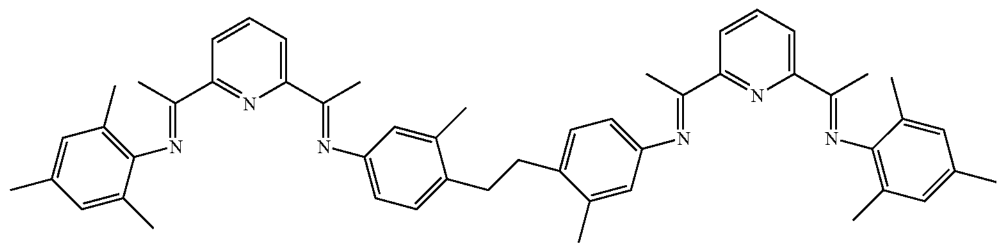 |

-continued

| NUMBER | STRUCTURE |
|---|---|
| IX | 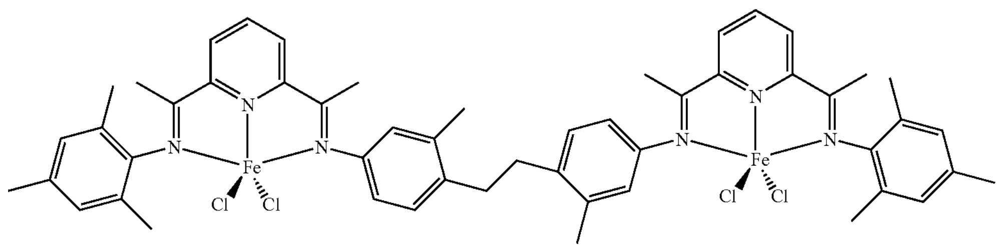 |
| X | 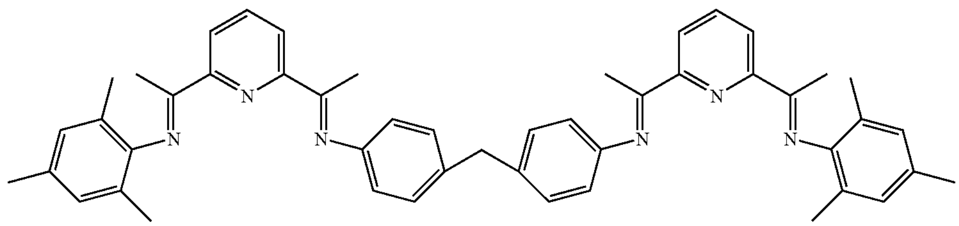 |
| XI | 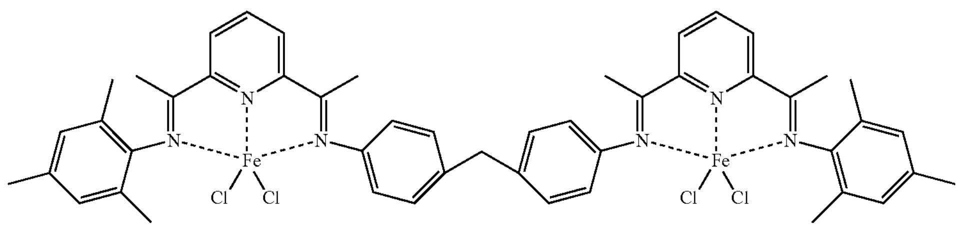 |
| XII | 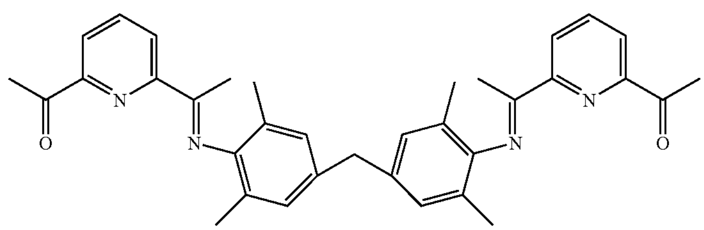 |
| XIII | 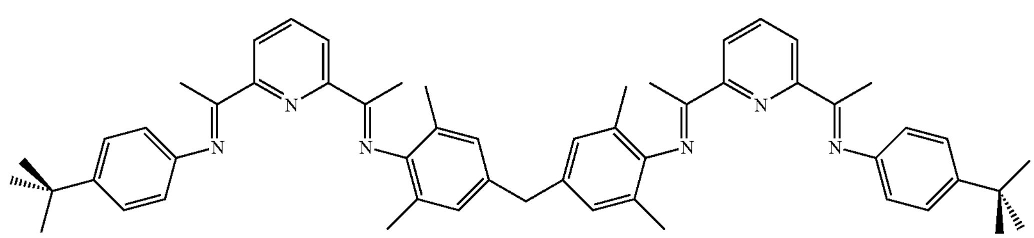 |
| XIV | 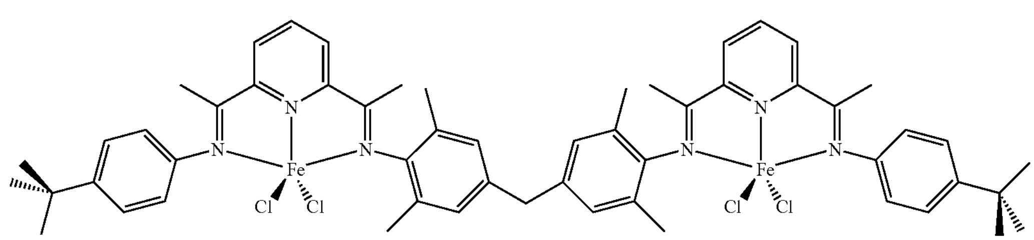 |

In the chemical structures of Table 1, groups represented by nothing are hydrogen, and groups represented by a single line, broken line, or bold line are methyl.

In an embodiment, a method for preparing a polymerization catalyst system is provided. The method comprises a coordination reaction between a hexadentate ligand having chemical structure I or II, and having embodiments as set out previously in this application, and a metal salt. The result of the coordination reaction includes a hexadentate bimetallic complex having chemical structure III or IV, and having embodiments as set out previously in this application. The method further comprises generating a metal alkyl or metal hydride species, and contacting the catalyst system with one or more monomers under suitable reaction conditions to polymerize the monomer.

In another embodiment of the method for preparing a polymerization catalyst, olefins may or may not be present during generation of a metal alkyl or metal hydride species. In another embodiment, the metal hydride or metal alkyl species is generated by a Lewis acid or a combination of a Lewis acid and alkylating agent. Examples of Lewis acids include $(C_6F_5)_3B$ or $(C_6H_5)_3B$. An example of a metal hydride is $NaBH_4$. In another embodiment, the metal hydride or metal alkyl species is generated by an alkyl aluminum compound such as, for example, triethylaluminum (TEA). In another embodiment, the metal hydride or metal alkyl species is generated by an alkyl aluminoxane such as a methyl-aluminoxane (MAO). In another embodiment, the metal hydride or metal alkyl species is generated by a combination of Lewis acids, alkyl aluminums, or alkyl aluminoxanes.

EXAMPLES

Example 1

1.00 g (3.57 mmol) of monoketone 5, which is represented by structure XV:

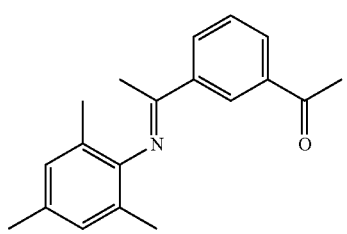

XV 0.34 g (1.42 mmol) of 4,4'-ethylenedi-m-toluidine, and 25 mg of p-toluenesulfonic acid were added to a flask in a drybox. A stirbar was added, followed by addition of 30 ml of anhydrous toluene. The reaction was stirred while being refluxed for 5 hours under inert atmosphere. The reaction was allowed to cool, was filtered to remove a very small amount of dark precipitate, and the solvent was then removed in vacuo. Ethanol was added to the remaining oil, and the resultant solid (426 mg, 39%) was isolated by filtration and identified by $^1H$ and $^{13}C$ NMR as chemical structure VIII (purity ~95%).

Example 2

Chemical structure VIII (150 mg, 0.196 mmol) and iron (II)chloride tetrahydrate (0.372 mmol) were added together in a small flask with a stirbar in a drybox. 10 ml of anhydrous THF was added, and the reaction was allowed to stir for 18 hours. Pentane was added, and the reaction was filtered and washed with pentane to give 182 mg (95% yield, assuming two equivalents of THF per complex molecule) of chemical structure IX.

Example 3

4.24 g (15.1 mmol) of monoketone 5, represented by structure XV, and 1.42 g (7.17 mmol) of 4,4'-methylenedianiline were dissolved in 50 ml of anhydrous toluene in a drybox. After dissolution of the solids, 3A molecular sieves were added and the solution was allowed to sit for 18 hours. More molecular sieves were then added, followed by the addition of 4 drops of sulfuric acid. The reaction was refluxed for 3 hours, allowed to cool, and then filtered. The solvent was removed in vacuo, and ethanol was added. The flask was placed in a freezer at 0° C. overnight, and 1.04 g (19%) of solid was removed by filtration after 1 day and identified by $^1H$ NMR as chemical structure X (~95% pure).

Example 4

2,6-Diacetylpyridine (10.0 g, 61.0 mmol) and 4,4'-methylenebis(2,6-dimethylaniline) (6.24 g, 24.5 mmol) were dissolved in 300 ml of ethanol in an open beaker. 5 drops of acetic acid were added, and the reaction was allowed to sit at 25° C. for several days. Several crops of crystals were collected (12.2 g, 91%), washed with cold ethanol, and identified by $^1H$ NMR as chemical structure XII.

Example 5

Chemical structure XII (2.0 g, 3.67 mmol) and 4-t-butylaniline (1.8 ml, 11.3 mmol) were dissolved in 50 ml of anhydrous toluene in a flask in a drybox. 3A molecular sieves were added, and the solution was allowed to sit for 3 days. More molecular sieves were added, followed by the addition of 2 drops of sulfuric acid. The reaction was refluxed for 3 hours, allowed to cool, and filtered. The molecular sieves were washed with ethanol. The solvent was removed by filtration, ethanol was added, and a solid was collected by filtration. This solid was recrystallized from an ethanol cyclohexane mixture and identified by $^1H$ NMR as chemical structure XIII (490 mg, 17% yield, ~95% purity).

Example 6

Chemical structure XIII (300 mg, 0.372 mmol) and iron (II)chloride tetrahydrate (148 mg, 0.744 mmol) were added together in a small flask with a stirbar in a drybox. 15 ml of anhydrous THF was added, and the reaction was allowed to stir for 18 hours. Pentane was added, and the reaction was filtered and washed with ether and pentane to give 350 mg (78% yield, assuming two equivalents of THF per complex molecule) of chemical structure XIV.

Example 7

Under semi-continuous operating conditions, 120 grams of cyclohexane were pumped into a 1 liter reactor, and the reactor was pressurized with ethylene. Next pumps were used to quickly transfer the first hour's amounts of chemical structure XIV and triethylaluminum (TEA) to the reactor. The hourly flow rates were then set for the catalyst and co-catalyst, and the reaction was allowed to exotherm to the desired run temperature. The reaction was stopped 150 minutes after reaching 50° C. The data in the following table represent the last sample taken before stopping the reaction.

| Solvent (120 g) | CyH |
|---|---|
| Catalyst | XIV |
| Flowrate (mg/hr) | 0.2 |
| Yield (g) | 374 |
| lb prod/lb Al | 5004 |
| lb prod/lb Fe cat (×10³) | 509 |
| Al:Fe ratio | 2000 |
| K(C20/C18) | 0.68 |
| K(C16/C14) | 0.69 |
| K(C10/C8) | 0.69 |
| P ethylene (psig) | 500 |
| 1-hexene Purity | 99.34 |
| C6 % Branched Alpha Olefins (BAO) | 0.17 |
| C6 % Paraffin | 0.21 |
| 1-octene Purity | 99.05 |
| C8 % Branched Alpha Olefins (BAO) | 0.29 |

FIG. 1 is a chart illustrating the catalyst's high selectivity for ethylene relative to higher olefins.

While the present invention has been illustrated and described in terms of particular apparatus and methods of use, it is apparent that equivalent techniques and ingredients may be substituted for those shown, and other changes can be made within the scope of the present invention as defined by the appended claims.

The particular embodiments disclosed herein are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

I claim:

1. A ligand for polymerization of olefins having chemical structure I:

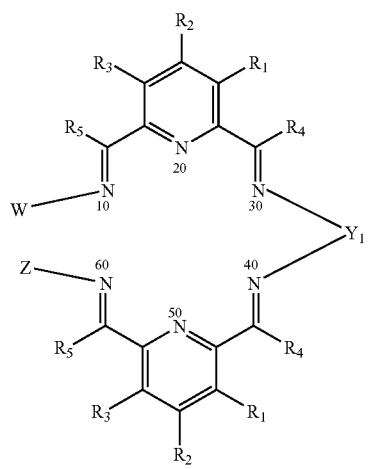

wherein $R_1$, $R_2$, and $R_3$ are each indenpendently hydrogen, hydrocarbyl, substituted hydrocarbyl, or an inert functional group;

$R_4$ and $R_5$ are each independently hydrogen, hydrocarbyl, an inert functional group, or substituted hydrocarbyl; and $Y_1$ is a structural bridge, and W, $Y_1$, and Z are independently hydrogen, hydrocarbyl, an inert functional group, or substituted hydrocarbyl having from about 0 to about 30 carbon atoms; and wherein $Y_1$ is cyclohexane.

2. A ligand for polymerization of olefins having chemical structure II:

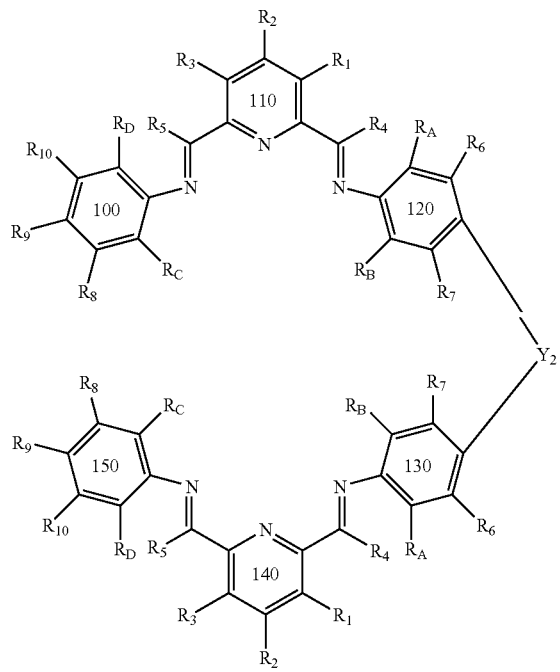

wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl;

$R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and more particularly may be a bond, a hydrocarbyl group comprising from about 2 to about 20 carbon atoms, ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring; and wherein $Y_2$ connects rings at their respective para positions and $R_7$ is located at the respective meta positions.

3. A ligand for polymerization of olefins having chemical structure II:

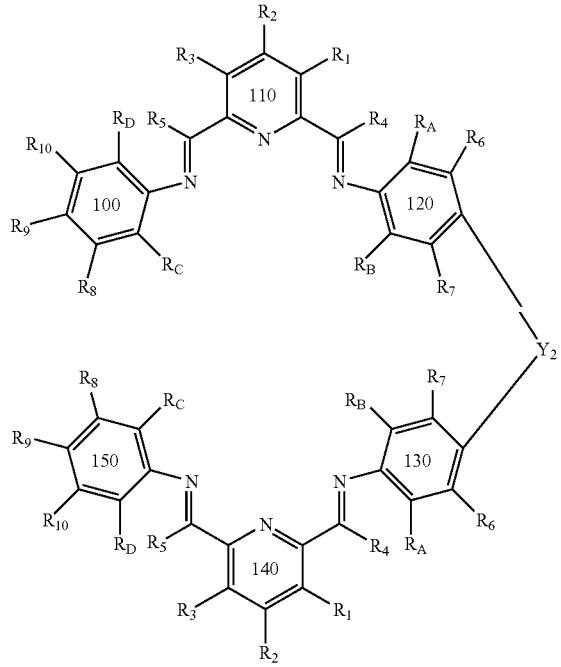

wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl;

$R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or tertiary carbon group;

$Y_2$ is a structural bridge between two halves of the structure, and more particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring; and wherein $R_A$ and $R_B$ are hydrogen; and $R_C$ and $R_D$ are independently methyl, ethyl, propyl, or isopropyl.

4. The ligand of claim 3 wherein $R_C$ and $R_D$ are both methyl.

5. A ligand for polymerization of olefins having chemical structure II:

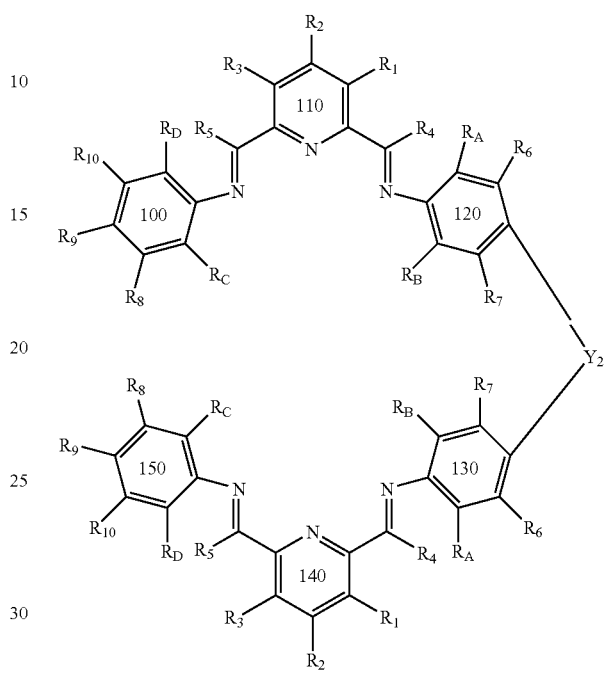

wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl;

$R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and more particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring; and wherein $R_C$ and $R_D$ are hydrogen; and $R_A$ and $R_B$ are independently methyl, ethyl, propyl, or isopropyl.

6. The ligand of claim 5 wherein $R_A$ and $R_B$ are both methyl.

7. A ligand for polymerization of olefins having chemical structure II:

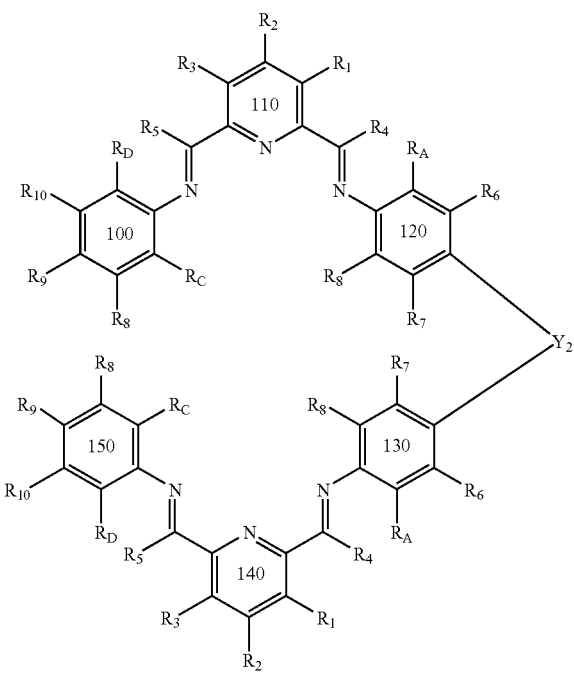

wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl;

$R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and more particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring; and wherein $R_A$ and $R_D$ are hydrogen; and $R_B$ and $R_C$ are independently methyl, ethyl, propyl, or isopropyl.

8. The ligand of claim 7 wherein $R_B$ and $R_C$ are both methyl.

9. A ligand having chemical structure VIII:

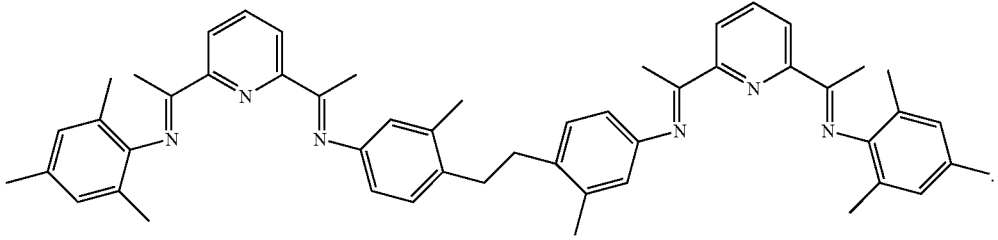

10. A ligand having chemical structure X:

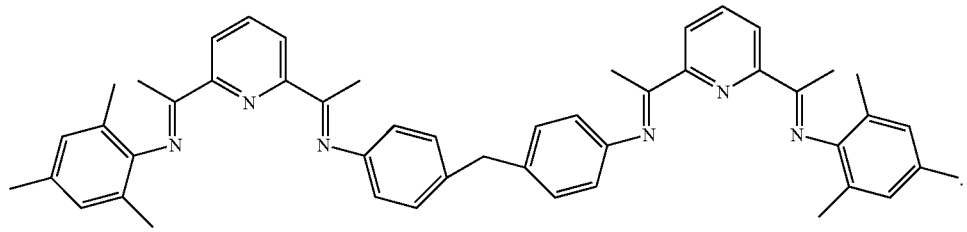

11. A ligand having chemical structure XII:

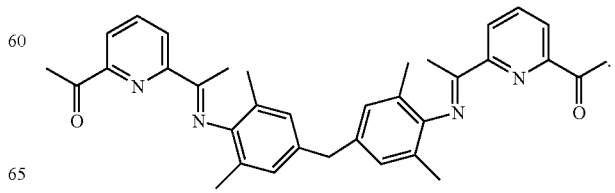

12. A ligand having chemical structure XIII:

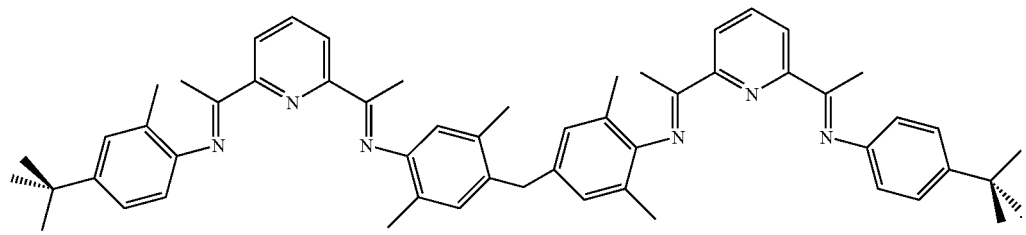

13. A ligand for polymerization of olefins having chemical structure II:

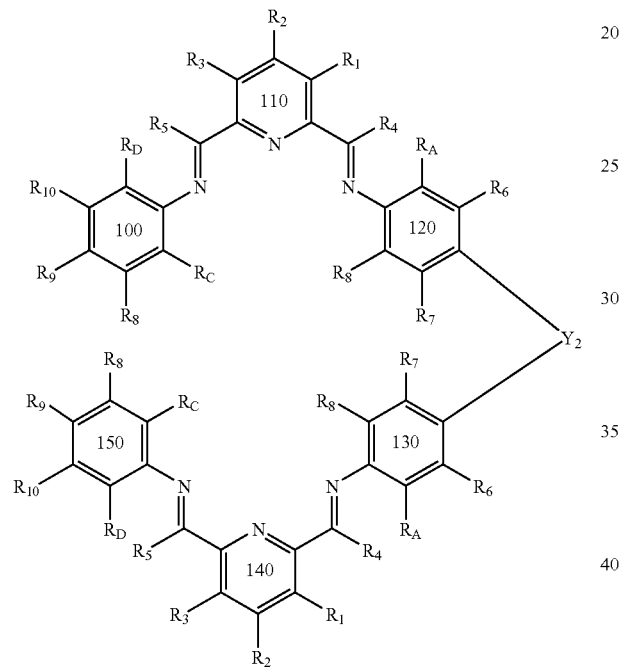

wherein $R_1$, $R_2$, and $R_3$ are each independently hydrogen, hydrocarbyl, substituted hydrocarbyl, or an inert functional group;

$R_4$ and $R_5$ are each independently hydrogen, hydrocarbyl, an inert functional group, or substituted hydrocarbyl;

$R_6$, $R_7$, $R_8$, $R_9$, and $R_{10}$ are each independently hydrogen, hydrocarbyl, an inert functional group, or substituted hydrocarbyl;

$R_A$, $R_B$, $R_C$, and $R_D$ are each independently hydrogen, fluorine, an inert functional group, a primary carbon group, a secondary carbon group, or a tertiary carbon group;

$Y_2$ is a structural bridge between two halves of the structure, and mare particularly may be a bond, a hydrocarbyl group comprising from about 0 to about 20 carbon atoms, methylene ($CH_2$), ethylene ($C_2H_4$), or an inert functional group; and any two of $R_A$, $R_6$, $R_7$, $R_B$, $R_C$, $R_8$, $R_9$, $R_{10}$, and $R_D$, or any portion of $Y_2$, vicinal to one another, taken together may form a ring;

wherein $Y_2$ connects rings at their respective para positions and $R_7$ is located at the respective meta positions; and wherein the pendant groups are as defined above, with the exception that:

when $R_A$ is a primary carbon group, then none, one, or two of $R_B$, $R_C$, and $R_D$ are primary carbon groups, secondary carbon groups, phenyl, substituted phenyl, or inert functional groups, and the remainder of $R_B$, $R_C$, and $R_D$ are hydrogen or fluorine; or when $R_A$ is a secondary carbon group, then none, one, or two of $R_B$, $R_C$ and $R_D$ are primary carbon groups, secondary carbon groups, phenyl, substituted phenyl, or inert functional groups, and the remainder of $R_B$, $R_C$, and $R_D$ are hydrogen or fluorine; or when $R_A$ is a tertiary carbon group, then none or one of $R_B$, $R_C$, and $R_D$ are tertiary, phenyl, or substituted phenyl, and the remainder are hydrogen or fluorine; and when $R_C$ is a primary carbon group, then none, one, or two of $R_A$, $R_B$, and $R_D$ are primary carbon groups, secondary carbon groups, phenyl, substituted phenyl, or inert functional groups, and the remainder of $R_A$, $R_B$, and $R_C$ are hydrogen or fluorine; or when $R_C$ is a secondary carbon group, then none, one, or two of $R_A$, $R_B$ and $R_D$ are primary carbon groups, secondary carbon groups, phenyl, substituted phenyl, or inert functional groups, and the remainder of $R_A$, $R_B$, and $R_D$ are hydrogen or fluorine; or when $R_C$ is a tertiary carbon group, then none or one of $R_A$, $R_B$, and $R_D$ are tertiary, phenyl, or substituted phenyl, and the remainder of $R_A$, $R_B$, and $R_D$ are hydrogen or fluorine.

* * * * *